United States Patent [19]

Sandrock et al.

[11] 4,227,810
[45] * Oct. 14, 1980

[54] CUVETTE AND METHOD OF USE

[75] Inventors: Harold E. Sandrock, Rockville Centre; Morris W. Leen, Yorktown Hgts.; Edward W. Stark, Garden City, all of N.Y.

[73] Assignee: Technicon Instruments Corporation, Tarrytown, N.Y.

[*] Notice: The portion of the term of this patent subsequent to Nov. 30, 1993, has been disclaimed.

[21] Appl. No.: 872,404

[22] Filed: Jan. 26, 1978

Related U.S. Application Data

[62] Division of Ser. No. 739,902, Nov. 8, 1976, Pat. No. 4,083,638, which is a division of Ser. No. 604,526, Aug. 14, 1975, Pat. No. 3,994,594.

[51] Int. Cl.$^2$ ............................................. G01N 1/10
[52] U.S. Cl. ..................... 356/246; 250/576
[58] Field of Search ................ 356/246; 250/576; 23/253 R, 259

[56] References Cited

U.S. PATENT DOCUMENTS

| | | | |
|---|---|---|---|
| 3,691,017 | 9/1972 | Brown et al. | 356/246 X |
| 3,795,451 | 3/1974 | Mailen | 356/246 |
| 3,799,742 | 3/1974 | Coleman | 356/246 X |
| 3,865,548 | 2/1975 | Padawer | 356/246 X |
| 3,961,899 | 6/1976 | Trivedi et al. | 356/246 X |

Primary Examiner—F. L. Evans
Assistant Examiner—Matthew W. Koren
Attorney, Agent, or Firm—S. P. Tedesco

[57] ABSTRACT

A multichamber cuvette for maintaining in independent and separate condition at least two reactants until such time that it is desired to mix them for reaction with each other and a reactant liquid sample while in the cuvette for analysis in the cuvette, and a method of use of such cuvette. There is provided a cuvette body of a suitable plastic defining at least two chambers interconnected by a passageway of relatively small cross section having at least the end portion thereof of capillary size to prevent under many circumstances, as by surface tension, accidental mixture of liquid reactants in the chambers. If there is a substantial head of liquid in one chamber and/or a risk of impact of the cuvette with an external foreign object, sufficient to break such surface tension, an air lock in the passageway when the latter is below the liquid levels in the chambers prevents such accidental mixture. A baffle in the passageway enhances separation of liquids and/or solid substances in the chambers. The chambers are open-topped, and a unitary probe-wiping multi-ply laminated cover of a type puncturable by a probe extends over the chambers closing them from the external environment. The laminated cover tends to be self-closing with reference to such punctures. One ply is of metal foil to act as a vapor seal and has an undercoating of a heat sealable material compatible with the body material and sealed thereto. The top ply is of a moisture-absorbent material which is secured to the foil ply by an intermediate plastic ply.

13 Claims, 21 Drawing Figures

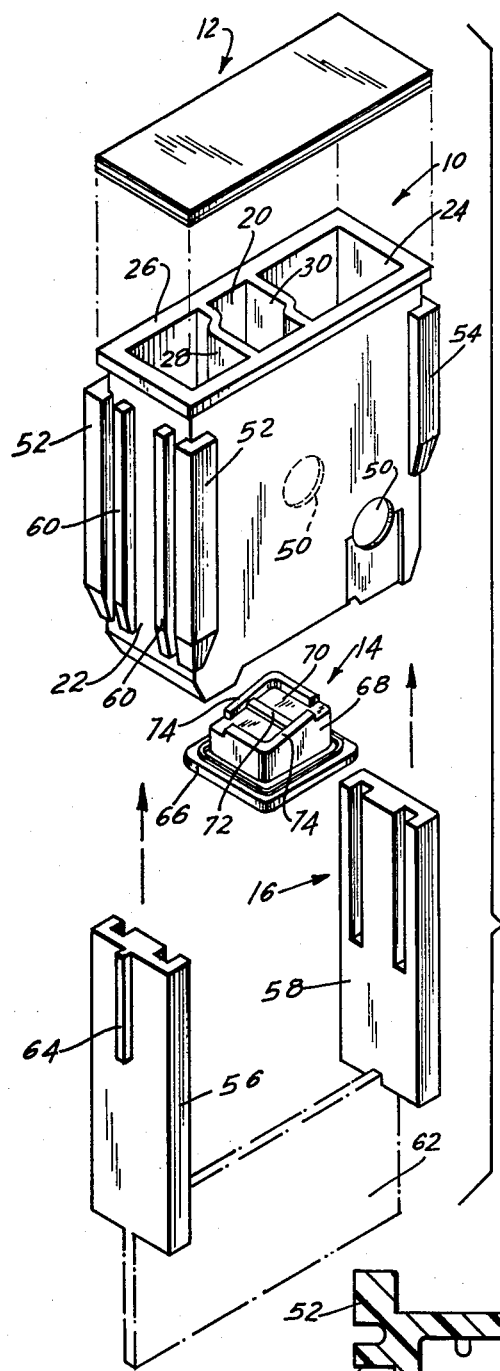
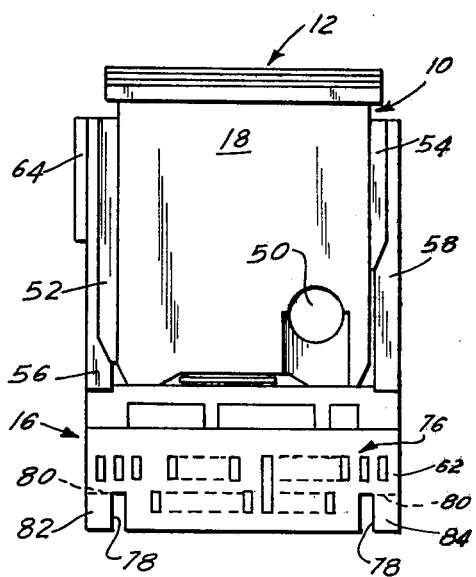
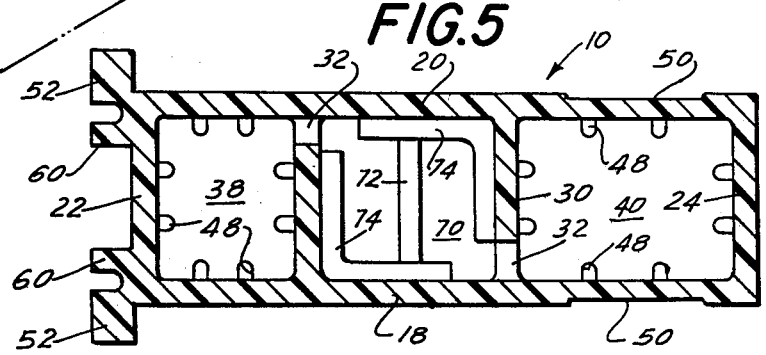

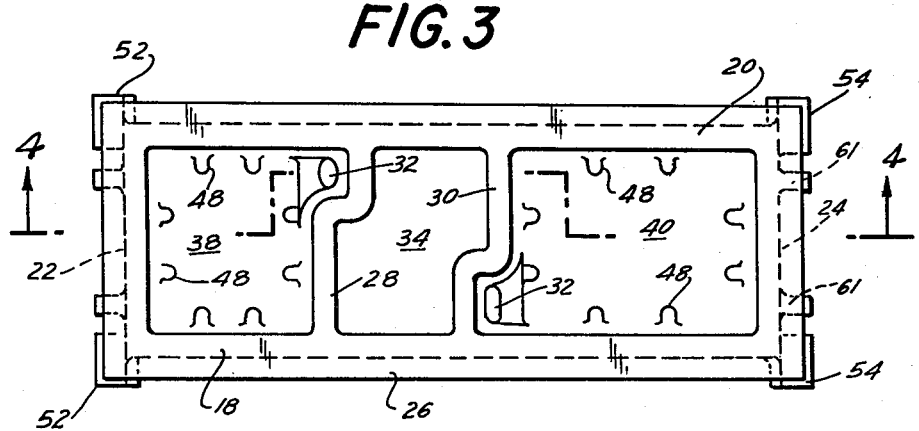
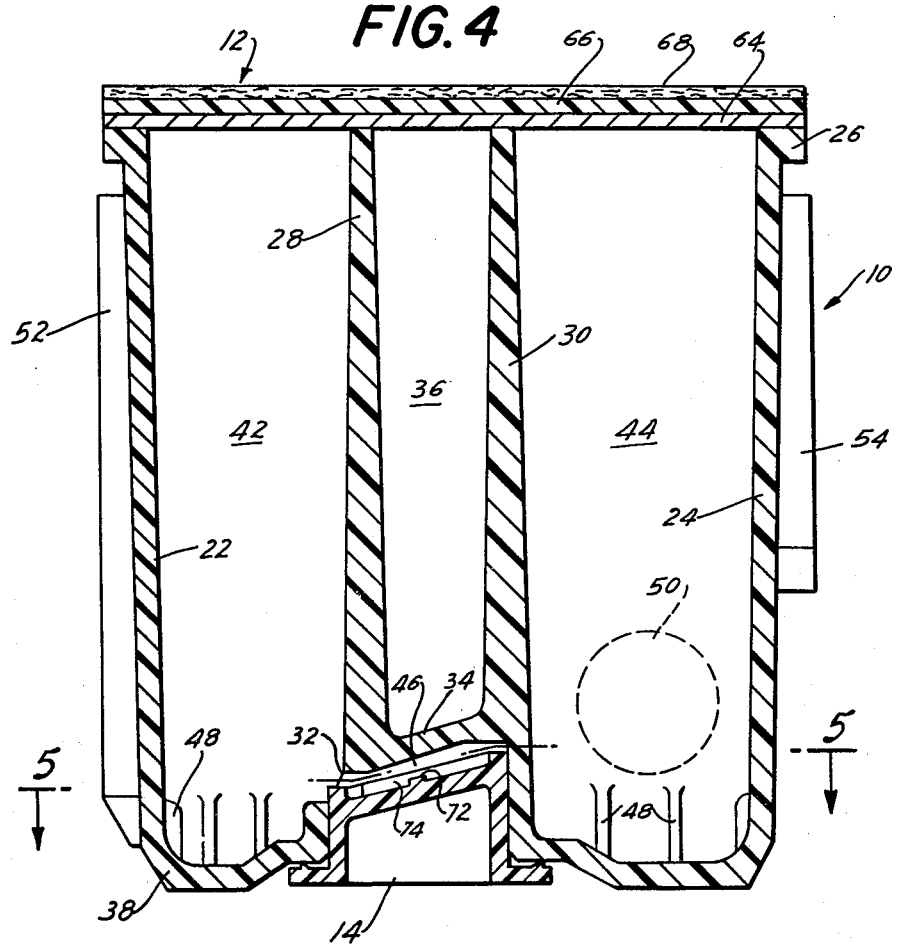

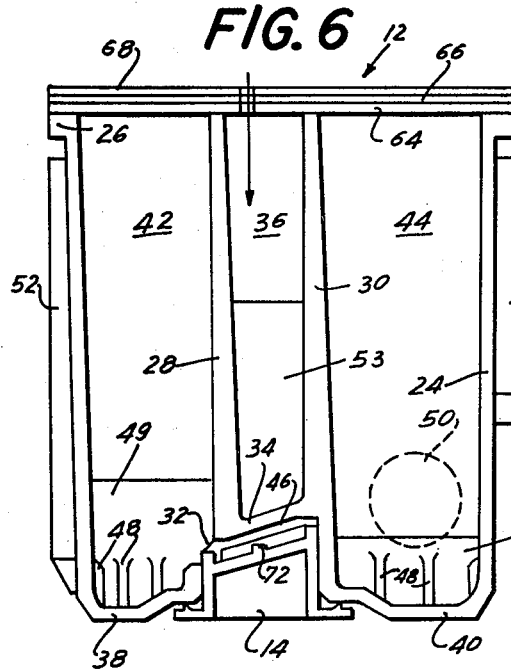
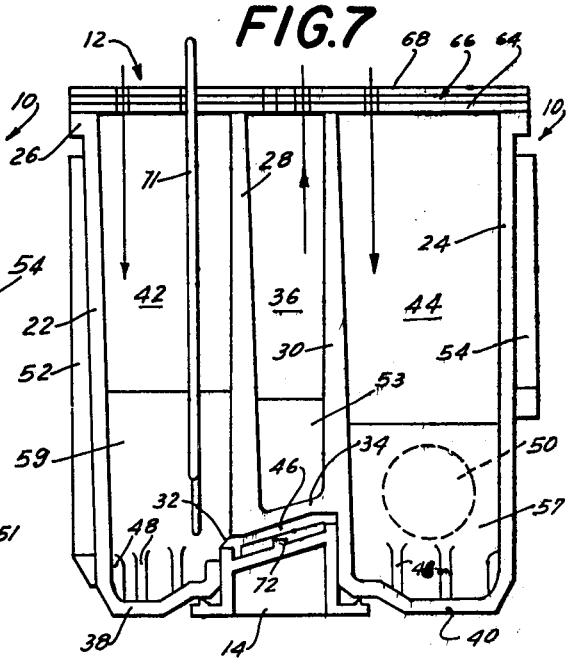
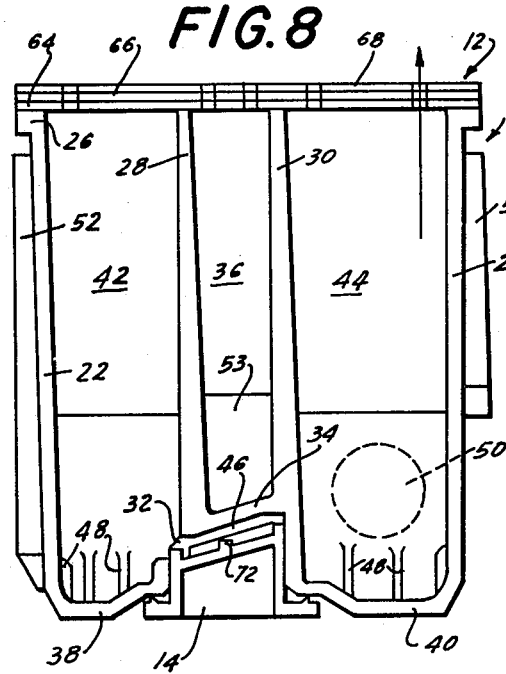
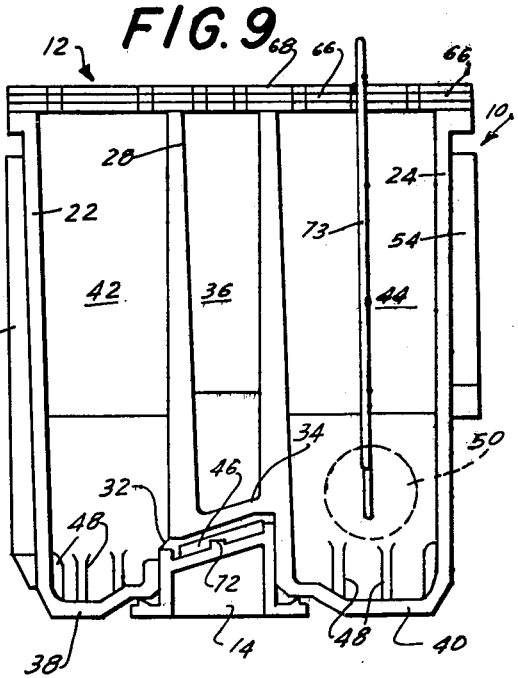

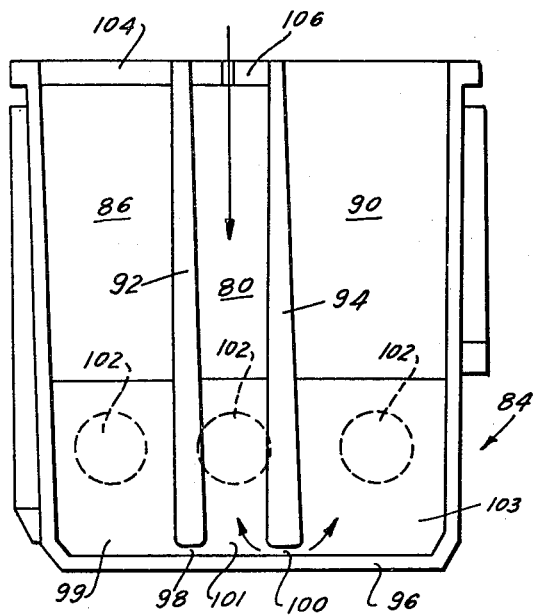
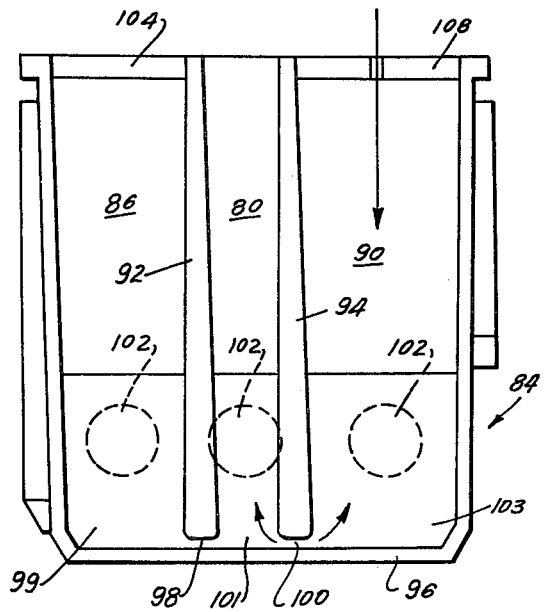
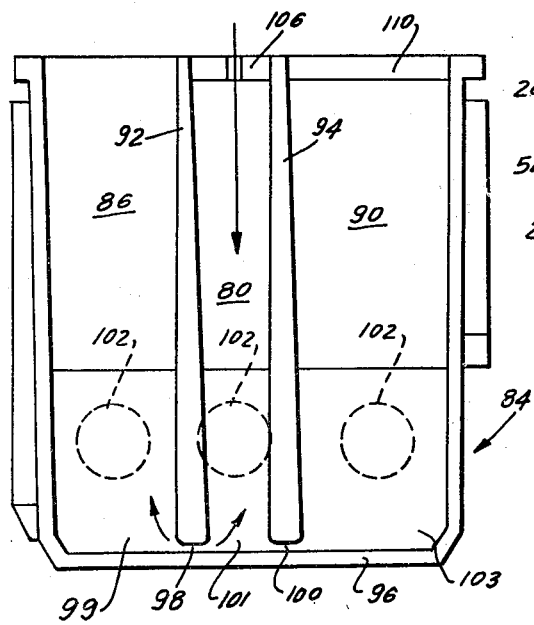
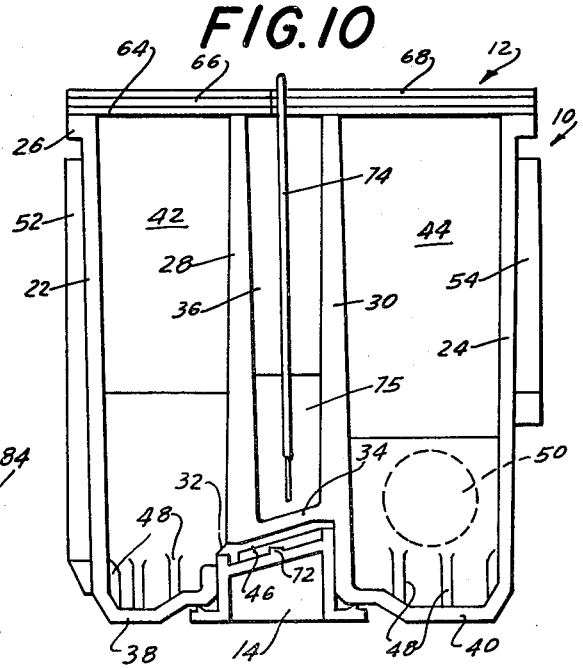

CUVETTE AND METHOD OF USE

This is a division of application Ser. No. 739,902, filed Nov. 8, 1976, now U.S. Pat. No. 4,083,638; which is a division of Ser. No. 604,526, filed Aug. 14, 1975, now U.S. Pat. No. 3,994,594.

BACKGROUND OF THE INVENTION

1. Field of the Invention

This invention relates to a multichamber cuvette and its use and relates more particularly to such cuvette which, while not limited thereto, is especially useful in analysis by optical density in an automated manner of a constituent of body fluids such as blood or urine for example.

2. Prior Art

Brown et al U.S. Pat. No. 3,691,017, Mailen U.S. Pat. No. 3,795,451 and Rosse et al U.S. Pat. No. 3,718,439 are typical of the prior art. Brown et al disclosed a multichamber cuvette for analysis of a constituent of interest in body fluids by an optical density determination in an automated manner. It was disclosed by Brown et al that a reaction may be measured in the cuvette at one point in its duration or at its end point or a reaction in the cuvette may be temperature-and-time dependent and of the type, measured over a period of time, indicating the quantity of the constituent of interest by the rate of the reaction. In accordance with Brown et al, in such kinetic or rate reaction analyses of an enzyme, a trigger or key reactant component, initially located in a first chamber in restricted communication with a second chamber, was of a substrate of an enzymatically catalyzed reaction with a component in the second chamber, and wherein, after a solvent medium had been introduced in the chambers to reconstitute the reagents previously in lyophilized form, a substance (liquid sample) comprising the catalyzing enzyme was introduced into the second chamber prior to forceful injection thereinto of the key substance for the reaction to proceed under temperature-controlled conditions.

The cuvette was found to have many drawbacks in practice adversely affecting analysis among which, of a more serious type, were that the cuvette did not provide a uniformly precise viewing length of the reaction mixture, portions of the minute liquid volumes utilized in the cuvette evaporated to the atmosphere, the reactants were not sufficiently isolated to prevent comingling and contamination was found to exist in the chambers of the cuvette during use. The contamination was with reference to sample carryover, in dispensing using the same probe of one sample utilized in one cuvette, to the next following dispensed sample utilized in another cuvette.

The design of the cell was such that the liquids which required separation prior to intentional mixing in a cuvette were separated primarily only by a restricted passageway formed by two opposing ribs and providing an opening (1.5 mm×2.5 mm) of sufficient size that water flowed therethrough on reconstitution of the lyophilized reagents. The passageway was of an axial length of only the thickness of a relatively thin rib or partial partition, though the last-mentioned patentees taught that the length of the passageway could be extended. Such being the case, the aforementioned reconstituted reagents in the two chambers of the cuvette were in liquid interfacing relation within the cuvette prior to intentional mixing of the reagents for the reaction to proceed under controlled conditions. Statements of the patentee to the contrary notwithstanding, this enabled a small quantity of one of the liquid reagents to migrate into and commence reaction with the other liquid reactants during the period of time when it was desired to maintain the liquids in complete isolation from one another, as during incubation, to prevent their reaction with one another. It was found that migration by diffusion of only 3% of the reconstituted aforementioned trigger or key component in liquid form into the aforementioned second chamber was sufficient to invalidate an analysis. Such migration might be occasioned by jarring the cuvette. Further, in accordance with Brown et al, only a single diluent was used in a single injection to reconstitute the different reagents in both chambers and any buffer substances in a communicating buffer section within the second chamber. This injection was made into the second chamber for partial retention and flow therethrough and the buffer section into the first chamber for retention therein, resulting in a high degree of risk of comingling of the reagents.

In the manufacture of the cuvette, liquid reagents were introduced onto plural surfaces of the cuvette and lyophilized in situ. The design attempted to separate in the cuvette such reagents while in lyophilized form but in fact permitted comingling of such lyophilized reagents in a manner to prejudice analyses. Such lyophilized reagents were later reconstituted by addition of a suitable solvent after assembly of the dual sections in the cuvette body. The chambers were not sealed from the external environment in use, permitting evaporation of a liquid contents. Moreover, as the windowed light path through the cuvette for viewing the reaction therein was provided in part in one of the dual sections and in part in the other, the combined tolerances to which the sections were manufactured resulted in considerable variation in light path length through the reaction, adversely affecting the precision of analysis. Further, the cuvette exhibited poor heat transfer, and was difficult and expensive to manufacture with the packaged reagents.

Rosse et al U.S. Pat. No. 3,718,439 discloses a hermatically sealed cuvette body defining three reactant-receiving chambers having no fluid communication therebetween and each provided with a pair of optical windows, the windows of the pairs being uniformly spaced.

Mailen U.S. Pat. No. 3,795,451 disclosed a rotor for loading and mixing sample and reagent liquids for use in a photometric analyzer of the rotary sample-analysis cuvette type. Inner and outer concentric arrays of loading cavities were disposed within the rotor on a one-to-one basis centripetal to an array of sample analysis cuvettes. Liquid communication was provided by capillary-sized passageways between the respective sample, reagent and analysis cavities and cuvettes upon rotation of the rotor, while intercontact of the liquids in the respective cavities was prevented under static loading conditions. The aforementioned respective passages between the inner and outer cavities were each provided with an air lock in the form of a bubble trap under static conditions.

The present invention overcomes difficulties with the prior art.

SUMMARY OF THE INVENTION

One object of the invention is to provide a multichamber cuvette for maintaining in independent and separate condition at least two reactants until such time that it is desired to mix them for reaction with each other and a reactant liquid sample while in the cuvette for analysis in the cuvette, and a method of use of such cuvette.

Another object is to provide in such a cuvette a body of a suitable plastic defining at least two chambers interconnected by a passageway of relatively small cross section having at least the end portions thereof of capillary size to prevent under many circumstances, as by surface tension, accidental mixture of liquid reactants in the chambers. If there is a substantial head of liquid in one chamber and/or a risk of impact of the cuvette with an external foreign object, sufficient to break such surface tension, an air lock in the passageway when the latter is below the liquid level in the chambers prevents such accidental mixture. A baffle in the passageway enhances separation of the liquids and/or solid substances in the chambers.

A further object is to provide in a cuvette, in which the body is open-topped, a probe-wiping multi-ply cover of a laminated type puncturable by a probe and closing the body from the external environment. The laminated cover tends to be self-closing with reference to such punctures. One ply is of metal foil to act as a vapor seal and has an under coating of a heat sealable material compatible with the body material and sealed thereto. The top ply is of a moisture-absorbent material which is secured to the foil ply by an intermediate plastic ply.

BRIEF DESCRIPTION OF THE DRAWINGS

In the drawings:

FIG. 1 is a front elevational view illustrating a cuvette embodying the invention;

FIG. 2 is an exploded isometric view of the cuvette;

FIG. 3 is a top plan view of the body of the cuvette with the cover removed;

FIG. 4 is a median sectional view of the cuvette body and the cover;

FIG. 5 is a sectional view taken on line 5—5 of FIG. 4;

FIGS. 6-9 are views similar to FIG. 4 illustrating progressive stages of use of the cuvette;

FIG. 10 is a view similar to FIG. 6 illustrating a different use of the cuvette;

FIGS. 11-13 illustrate a modified form of the cuvette body (with a cover therefor removed) and different stages of use of such cuvette;

DETAILED DESCRIPTION OF PREFERRED EMBODIMENTS

Figures 14, 15:
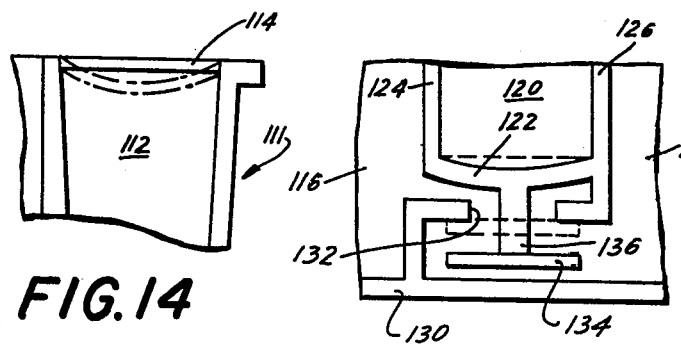
FIGS. 14-19 are fragmentary, elevational views illustrating further modifications of the cuvette.

In the form of FIGS. 1 through 10, there is best shown in FIGS. 1 and 2 the general organization of the parts of the cuvette in which the cuvette body is indicated generally at 10, the cover at 12, the bottom cap at 14 and the carrier at 16. The body 10 is formed of a suitable transparent plastic material of optical quality. The material may be styrene or acrylic resin. For purposes hereinafter, the bottom cap 14 may be considered an integral part of the body as it is permanently secured thereto in fluid-tight relation as by ultrasonic welding in a location which will be apparent hereinafter. The part 10 is cast in one piece as is the part 14. The body is generally oblong in cross section, having a front 18, back 20 and side walls 22, 24. The body is upstanding, open at the top, and has a planar peripheral flange 26 at the top.

The body 10 is partitioned in part by vertically extending laterally spaced partitions 28, 30 between the front and back, each having an axially offset portion shown in FIGS. 2 and 3. The partitions 28, 30 are so arranged that such offsets are diagonally opposite one another to facilitate molding of the body with orifices 32 (FIG. 3) thereinto near the bottom thereof, which in this illustrated form by way of example are diagonally opposite one another. A generally horizontal partition 34 extends between the partitions 28, 30 in the lower region thereof as shown in FIGS. 3 and 4, to form the bottom of an upper central chamber 36, which in the condition of FIG. 2 is open at the top, and a downwardly extending recess in the body to receive cap 14. The orifices 32 open laterally into the recess. The construction of the bottom of the body 10 is best shown in FIGS. 3 and 4 wherein it is shown that the sidewalls 22, 24 have at their lower portions generally horizontally extending portions 38, 40, respectively, merging into the integral vertical partitions 28, 30, respectively, and forming the bottoms of a first chamber 42 and a second chamber 44, respectively, at opposite sides of the central chamber 36. The cap 14 received in the aforementioned recess underlies the chamber 36 and forms with the aforementioned partition 34 a generally horizontally extending passageway 46 of relatively small cross section having its respective ends in communication with the aforementioned orifices 32, opening into its cap-receiving recess, to provide controlled communication between the first chamber 42 and the second chamber 44. The bottom-forming extensions 38, 40 are flat on the underside, as is the bottom cap 14, and flush with one another so that the body 10 may stand on a table surface. The lower portions of the sidewalls of the chambers 42, 44 are provided with internal, vertically arranged, laterally spaced ribs 48 as shown in the last-mentioned views. The body in the region of the second chamber 44 which is the viewing chamber is provided in the front and rear walls with registering window portions 50 for viewing a reaction in the second chamber 44 and designed to be placed in a light path of a photometric analyzer, not shown.

For cooperation with the carrier 16, the body 10 has, partly on the sidewall 22, a pair of vertical corner flanges 52 externally thereof, and a pair of corner flanges 54 partly on the wall 24 (FIG. 3). The corner flanges of each pair receive therebetween in sliding relation to the upright, generally planar flanges 56, 58 of the carrier 16. For such sliding receipt, the wall 22 of the body is provided with a pair of vertically extending, laterally spaced ribs 60, and the wall 24 is provided with shorter, vertically arranged ribs 61 for reception in complemental grooves in the carrier portions 56 and 58, respectively. Such ribs key the body in such a manner that it cannot be assembled to the carrier 16 backward. The carrier has a flange portion 62 of planar shape interconnecting the portions 56, 58 thereof as shown in FIG. 2, and the portion 56 of the carrier has a flange 64 thereon by which the assembled body and carrier may be properly oriented in a cuvette-receiving well in the photometric analyzer. Nonillustrated coacting detent means on the body 10 and the carrier 16 may secure the body 10 in assembled relation with the carrier 16 in the condition of FIG. 1.

Figure 20:
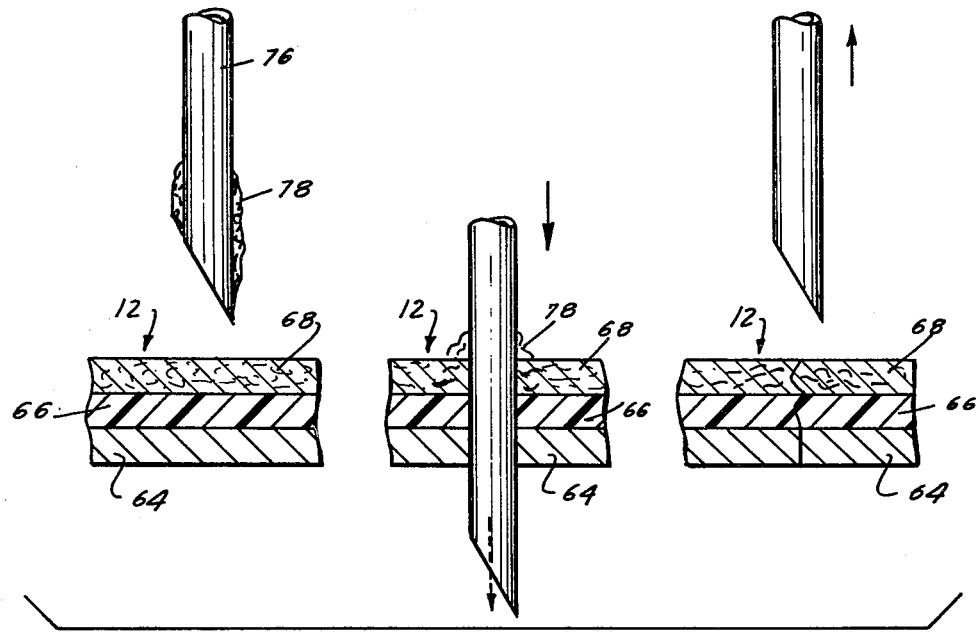
FIG. 20 is a fragmentary elevational view illustrating progressive steps of puncturing the cuvette cover with a probe, dispensing from the probe within the cuvette and withdrawal of the probe.
Figure 21:
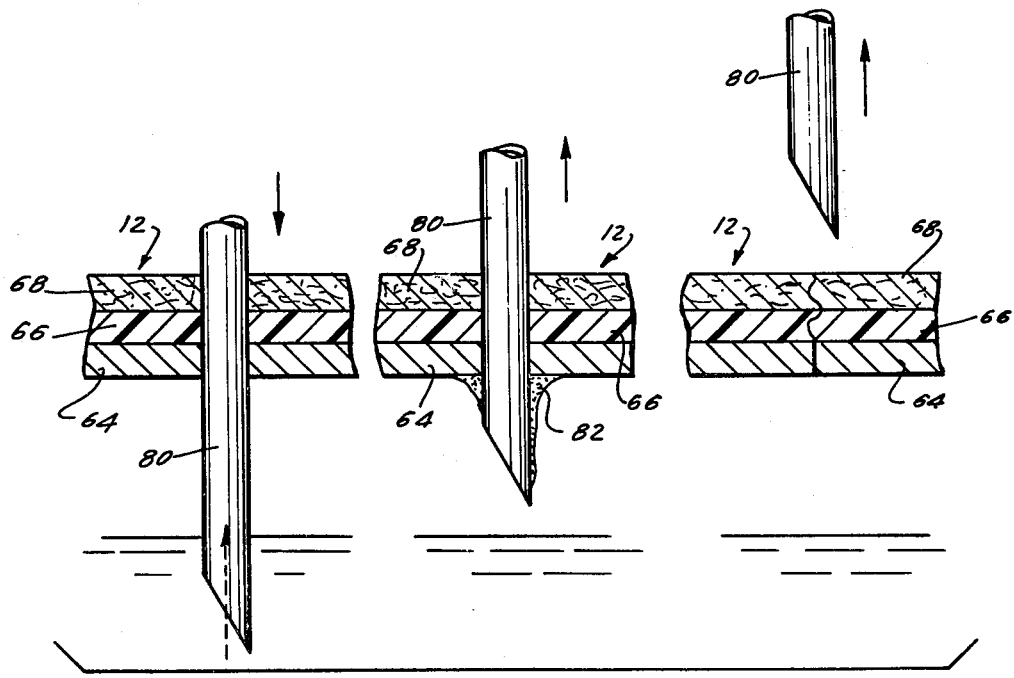
FIG. 21 is a view similar to FIG. 20 but illustrating progressively a probe aspirating liquid from the cuvette, partial withdrawal of the probe and complete withdrawal of the probe.

In the assembled condition, the cover 12 is secured to the aforementioned planar flange 26 of the body in a permanent manner. The cover is of a multi-ply or laminated construction best shown in FIG. 4 and further illustrated in FIGS. 20 and 21. It comprises a lower ply 64 of a suitable metal foil forming a vapor barrier and having on its underside a coating of a heat sealable material compatible with the material of the body, the ply 64 being securing to the flange 26 by the last-mentioned coating, not shown. The cover comprises an intermediate ply 66 of plastic material suitable to bond to the top ply of moisture-absorbant material such as paper or a fibrous non-paper product (such as a non-woven fabric, #5008, sold by International Paper Co.) to the foil ply 64, the top ply being indicated at 68. Such intermediate ply 66 may be formed for example of polyethylene. The cover 12 is continuous in a manner to completely seal the top of the body 10 in a manner to close the chambers 42, 44 and 36 while providing a structure which may be punctured by probes such as shown in FIGS. 20 and 21 for dispensing and aspirating liquids as will appear hereinafter, and which laminated construction tends to be self-closing of such punctures.

The bottom cap 14 of the part 10, best shown in FIGS. 2, 4 and 5, is of a configuration therein illustrated, the cap being formed of the same material as the part 10. As shown in FIG. 2, the cap 14 has a bottom, horizontal attachment flange 26 which is generally square and a hollow, central, four-sided plug portion 68 extending upwardly from the flange 66 and having on the upper surface thereof an inclined surface portion 70 interrupted by an upstanding rib-like baffle 72 extending transversely of the cuvette body. As shown, such surface 70 is bounded in part by two oppositely arranged marginal portions 74 of the plug 68 which are L-shaped and define lateral boundary portions of the aforementioned fluid passage 46 between the first chamber 42 and the second chamber 44. As shown in FIG. 5, the ends of the L-shaped portions 74 are spaced apart in the region of the orifices 32 in the first and second chambers. As indicated in FIG. 4, the baffle 72 is of a lesser height than the portions 74 and does not approach occlusion of the passageway 46 which is sloped downwardly from right to left as indicated in this view. Also, as indicated in this view, the second chamber 44 may have a higher level of substance therein than the first chamber 42 without covering the near orifice 32. The orifices are of capillary size and circular, each having a dimension of approximately 0.025 inch. This size is such that when a liquid level in either or both of the first and second chambers is above the level of the respective orifices 32 and the passage 46 has no liquid therein, surface tension strongly resists passage of a liquid from either chamber into the passageway 46, depending on the surface tension of the liquid. The baffle 72 in the passage 46 may be 0.020 inch wide and 0.005 inch high. Further functions of the passageway 46 will appear hereinafter.

It is to be noted that the cuvette may consist only of the body 10, cover 12 and the bottom cap 14, that is, the carrier 16 may be omitted from the assembly. The last-mentioned assembly may be utilized in the photometric analyzer without need of the carrier 16, the main function of which is to carry an identification code below the body 10. Such identification code on the portion 62 of the carrier 16 is divided into sections as shown in FIG. 1 and may consist of a bar code indicated generally at 76 to identify the cuvette number and the chemistry for the analysis of the sample. Such bar code may be impressed into the material of the carrier portion 62 which material may be similar to that of the body 10 but does not require the optical characteristics of the body 10.

Each lower corner of the carrier portion 62 is notched, as at 78, and is provided with a horizontally extending weakened zone indicated by the broken line 80 so that either corner 82 or 84 may be broken off at such weakened zone by manipulation. If the corner tab 82 is broken off it indicates to the analyzer that the cuvette contains a sample reference of known values for calibration of the analyzer. If the corner tab 84 is broken off and not the tab 82, it indicates to the analyzer for calibration purposes that the cuvette contains reagents but no sample. If desired, such bar code 76 may include identification of the donor of a blood serum sample in the cuvette.

One typical use of the cuvette of FIGS. 1–9 is as follows. Such a use may be for the quantitative determination of lactic dehydrogenase in a sample of blood serum. The reagents employed are lactic acid, the key component or trigger for the reaction, and nicotinamide adenine dinucleotide (NAD) with an appropriate buffer (tris [hydroxymethyl] amino methane) in order to maintain pH. The lactic acid is deposited in solution in the first chamber 42 and the NAD/buffer in solution is deposited in the second chamber 44 in measured amounts, and, as these solutions fill these chambers over the level of the fluid passage 46, in this example, one having a considerable head while the other does not, the solutions are deposited substantially simultaneously thereby entrapping an air bubble in the passageway 46 which enhances the separation of the liquids by the surface tension of such liquids at the respective orifices 32. In this condition of the cuvette, the contents are lyophilized or freeze-dried in an atmosphere of some inert gas or dry air after which the cover 12 is secured in position on the cuvette body 10 in moisture-and-vapor-tight sealing relation. The reagents may be stored in this condition for considerable periods of time or the cuvette may be used immediately for analysis. The freeze-dried trigger reagent is indicated at 49 and the DPN reagent at 51 in FIG. 6. For such analysis, a quantity of a blood serum sample 53 is injected into the central chamber 36 by the use of a hypodermic needle, not shown, which penetrates the cover 12 for this dispensing purpose. The cuvette is then in the condition shown in FIG. 6. The cuvette may be stored in this condition for some time while refrigerated. As indicated in FIG. 6, the last-mentioned freeze-dried plugs of reagents 49, 51 are firmly supported in the bottoms of the chambers 42, 44 by the internal ribs thereof to which the plugs adhere. The freeze-dried reagents must be maintained in isolated condition, and, to this end, the baffle 72 in the passageway 46 affectively separates any freeze-dried reagents that may find their way into such passageway. This is also true of reactants in liquid form which may have low surface tension characteristics. While the reagent plug in the chamber 44 is shown in the last-mentioned view as being of a lesser height than the plug in the chamber 42, the conditions may be reversed in the chambers as they are in many instances of use. The construction of the inclined passageway 46 of the cuvette is such that the height of the liquid or the reagent plug in the chamber 44 may be higher than the liquid or the reagent 49 in the chamber 42 without either plug extending over the corresponding orifices 32. In the serum determination under discussion, the relative amounts of the serum, lactic acid reagent and the DPN reagent which enter into the aforementioned reaction have been disregarded in illustrating the heights to which the chambers 42 and 44 are filled, which heights are purely by way of illustration and not necessarily those used in practice in the particular analysis under discussion.

When the analysis is to be performed, a hypodermic needle punctures the cover 12 entering the chamber 36 to aspirate a predetermined amount of blood serum therefrom and the needle is withdrawn and subsequently repunctures the cover 12 in the area of the chamber 44 to introduce such blood serum into the last-mentioned chamber in a single injection together with a quantity of a diluent, which in this instance is water to reconstitute the freeze-dried reagent in the chamber, the mixture being indicated at 57 in FIG. 7. Substantially simultaneously with the dispensing in the chamber 44, a hypodermic needle, having punctured the cover 12 in the area of the chamber 42, dispenses water as diluent for this analysis in a proper volume in that chamber to reconstitute the solid reagent therein. The reconstituted reagent being indicated at 59 in this view. In certain other analyses, the diluent may be AMP. During these dispensing operations, an air bubble is trapped in the fluid passageway 46, and after such dispensing operations, the liquid levels in the cuvette may be those indicated in FIG. 7, the hypodermic needles having been withdrawn. The manner in which the needles or probes are wiped by the cover as illustrated in FIGS. 20 and 21 will be discussed hereinafter. The fluid contents are then during incubation brought up toward the temperature, usually 30° or 37° centigrade, at which the reaction is to take place under very finely controlled temperature conditions, see U.S. Ser. No. 620,462, Oct. 7, 1975. During this warm-up a temperature-sensing thermistor probe 71 punctures the cover 12 and is immersed in the liquid contents in the chamber 42 as shown in FIG. 7. Subsequent to such warm-up interval, the thermistor probe 71 is withdrawn from the cuvette and a probe, not shown, punctures the cover 12 and alternately introduces air thereinto and creates a partial vacuum therein to mix the contents of the chambers 42, 44 through the passageway 46 in the required number of cycles of such air introduction and partial vacuum. During this mixing, the baffle 72 in the passageway 46 enhances turbulence for better mixing. The last-mentioned probe is then withdrawn from the chamber 44 and the condition of the cuvette and its contents is that shown in FIG. 8.

The chemical reaction in the first chamber 42 and the second chamber 44 then takes place, the fluid contents having reached the proper controlled temperature. It is to be clearly understood that there is no mixing of the contents of the last-mentioned chambers until the aforementioned mixing which creates a sufficient pressure and vacuum to break the air lock in the passageway 46. This air lock is enhanced by the baffle 72 to which the air bubble tends to adhere.

When the mixing of the contents of the first and second chambers has been completed, any lactic dehydrogenase in the blood serum sample acts as a catalyst which catalyzes the reaction to form as reaction products pyruvic acid and DPN in the reduced form (DPNH). Since DPNH, which is produced as a reaction product, has a substantially higher optical density than does DPN, the rate of any increase in optical density is a function of the amount of lactic dehydrogenase in the blood serum sample. After the initiation of the reaction as the result of comingling of the substrate with the other reaction components, the reaction rate may be determined by placing the cuvette in a position, not shown, wherein light from a source at a wavelength of 340 nm passes through the transparent windows 50 of the cuvette and through the thickness of the reaction mass between the two windows. Any change in optical density per unit of time may be measured and the data thus obtained may be translated into values indicative of the quantity of lactic dehydrogenase contained in the blood serum samples. The data may be obtained from approximately 108 readings at intervals of 0.5 second. Further, included in such data is information concerning the estimated temperature of the reaction mixture in the chamber 44 at the time at which the readings were made by backward extrapolation. For this purpose a thermistor 73 is inserted through the cover 12 into the liquid contents in the chamber 44 for a temperature reading after the optical readings are complete, as shown in FIG. 9. Subsequent to the last-mentioned temperature reading, the probe is withdrawn and the cuvette may be disposed of in a convenient manner with its contents.

In the use shown in FIG. 10, the blood serum sample is not introduced into the central chamber 36 prior to being introduced into the chamber 44 but is introduced instead into the last-mentioned chamber with a diluent. Prior to such blood serum sample introduction into the chamber 44, a quantity of water 75 is introduced into the chamber 36 as by a hypodermic needle puncturing the cover 12 for example. After reconstitution of the reagents in chambers 42 and 44 and prior to mixing of the reaction components, a temperature-sensing thermistor probe 74 punctures the cover 12 and is immersed in the water in the chamber 36 during warm-up of the contents of the cuvette. This precludes any contamination of the contents of the chamber 42 by the thermistor probe 74.

The cooperation of the laminated cover with aspirating and dispensing probes and with the thermistor probe 71 to affect a wiping action on such probes and such thermistor will now be described as illustrated in FIGS. 20 and 21. In FIG. 20 there is illustrated a probe 76 having a dispensing function and which in the first elevated position thereof has a quantity 78 of a blood serum sample aspirated from a source, not shown, clinging thereto as it is about to puncture the cover 12, one of a series of samples to be dispersed into respective second chambers of a series of cuvettes. As the probe 76 descends and penetrates the cover 12, it leaves a puddle of such sample remainder 78 on the moisture-absorbent upper ply 68 of the cover. This ply quickly absorbs such puddle in a manner to transport and remove essentially all of such sample excess 78 from the vicinity of the probe 76, so that after descending into the cuvette and dispensing sample and upon withdrawal of the probe 76, the latter is in essentially externally clean condition when leaving the cover 12. The cover tends to close such puncture. In FIG. 21, probes 80 is shown having an aspirating function. The probe 80 on its downward movement through the cover 12 is immersed in the blood serum sample in a manner such that on withdrawal after sample aspiration the sample clings to the exterior thereof as at 82. This sample excess 82 on upward movement of the probe 80 is wiped off the probe by the cover, so that on complete withdrawal of such probe the exterior of the probe is essentially clean, and the cover 12 tends to close the puncture. Such wiping action of the cover 12 on all the probes prevents contaminating sample and reagent carryover between cuvettes. It is significant that the cuvette structure permits direct temperature-sensing of the compartmented liquids without contaminating carryover between cuvettes such as would interfere with the optically measured reaction. As previously indicated, the cuvette structure may omit the carrier 16, and, in such event, the sample chemistry code as well as other codes may appear on the front 18 of the cuvette body in the vicinity of the chamber 42 as on a label, for example.

In the modified form of the cuvette shown in FIGS. 11-13, the cuvette body, indicated generally at 84, is generally similar to the previously described body 10 but differs in the construction of the chamber-interconnecting fluid passageway of the cuvette. The body has a nonillustrated removable cover similar to the cover 12. The cuvette body 84 has laterally spaced vertically extending partitions 92, 94 formed integrally with the front and rear thereof and providing a central chamber 80, a first chamber 86 and a second chamber 90. The partitions 92, 94 terminate short of the bottom 96 of the cuvette body to provide a capillary-sized passageway 98 providing communication between chambers 80 and 86 and a capillary-sized passageway 100 providing communication between the chamber 80 and the chamber 90. In this form of the cuvette, each of the aforementioned chambers has a pair of optical windows therein, one being indicated at 102, for enabling viewing in the light path of the photometric analyzer the liquid contents of each chamber, one after another. For the sake of brevity of the description and simplicity, the level of the liquids 98, 101, 103 in the chambers 86, 80 and 90, respectively, are indicated to be the same, but it will be understood that the levels may be different from one another. The liquid 101 may be considered the sample, the liquid 99 the reconstituted trigger reagent and the liquid 103 the reconstituted remaining reagent. The cuvette in the condition of FIG. 11 but prior to any mixing of the liquid contents of the several chambers may be utilized in the aforementioned photometric analyzer for calibration purposes with reference to the sample in the chamber 80 and the two reagents in the chambers 89, 90, respectively. This is a significant advantage in analysis of the type under discussion.

When it is desired to mix the liquid contents of the chambers 80 and 90 through the passageway 100, closure 104 is applied to the top of the chamber 86 after removal of the cover, while a partial vacuum and air pressure are alternately applied to the chamber 80 through a restriction 106 in the top thereof, the top of the chamber 90 being open to the atmosphere. After such mixing, the mixture of the sample 101 and the reagent 103 is provided for calibration purposes by viewing such mixture either through the window 102 of the chamber 80 or the window 102 of the chamber 90. In similar fashion, the serum sample 101 in the chamber 80 and the reagent 103 in the chamber 90 may be mixed alternatively as shown in FIG. 12 for the same calibration of the analyzer. In the last-mentioned view, the closure 104 is positioned as previously indicated but the top of the central chamber 80 is open to the atmosphere, while a partial vacuum and air pressure are alternately applied to the chamber 90 through a restriction 108 in the top of the chamber 90. As previously indicated, this effects mixing of the fluid contents of chambers 80 and 90 through the passageway 100. If desired, the liquid reagent 99 of the first chamber 86 may be alternatively mixed with the blood serum sample 101 in the chamber 80 through the passageway 98 without initiating a reaction, that is, by excluding the reagent in the second chamber 90 by providing a closure 110 at the top of the chamber 90, allowing the first chamber 86 to communicate with the atmosphere through the open top thereof and alternately applying air pressure and partial vacuum through restriction 106 at the top of chamber 80, as indicated in FIG. 13. A calibration reading may then be obtained of the mixture of the blood serum sample and the key reagent component 99 in either the first chamber 86 or the central chamber 80. Subsequent, for example, to the last-mentioned reading, the closure 110 is removed from the cuvette of FIG. 13 and air pressure and a partial vacuum are applied as before to the central chamber 80 to mix (not shown) all of the liquid components in all chambers. On such mixing liquid flows between the chamber 80 and 90 through the passageway 100 and between the chambers 86 and 80 through the passageway 98. The top of the cuvette may then be recovered and the reaction may be read through any one of the windows 102 in the corresponding chamber of the cuvette.

In the modified form of the cuvette shown in FIG. 14, the cuvette, which is similar to that shown in the form of FIG. 11, has a body indicated generally at 111 defining a first chamber, not shown, similar to the chamber 42 and a second chamber 112 similar to the chamber 44 but having a probe-puncturable, self-closing diaphragm of rubber-like material, indicated at 114, extending across the upper end of the chamber 112. The cover, not shown, is removed prior to mixing of the aforementioned liquid contents (not shown), and to effect mixing the diaphragm 114 is repeatedly deflected to the extent shown in broken lines to effect pressure surges in the chamber 112 when the first chamber is open to the atmosphere and in communication with chamber 112.

In the modified form of the cuvette shown in FIG. 15, the body 115 of the cuvette defines a first chamber 116, a second chamber 118 and a central chamber 120 which has a deflectable bottom 122. Partitions 124, 126 partially define the chambers 116, 118 and 120 with the bottom 122 of the chamber 120 extending between such partitions. The partition 126 is extended downwardly below the bottom 122 and defines therein, in a portion integral with the bottom 130 of the cuvette body, and orifice 132 which is normally closed by a valve member 134 depending from the chamber bottom 122 as on a post 136. The orifice 132 provides the only means of communication between the chambers 116 and 118. To enable mixing of the liquids, not shown, in these chambers, the chamber bottom 122 is deflected downwardly by a force sufficient to open the valve member 134 to the position shown in FIG. 15. The valve member 134 remains in this position by the application of such force until such mixing as in the form of FIG. 1 is complete for the reaction to proceed.

Figure 16:
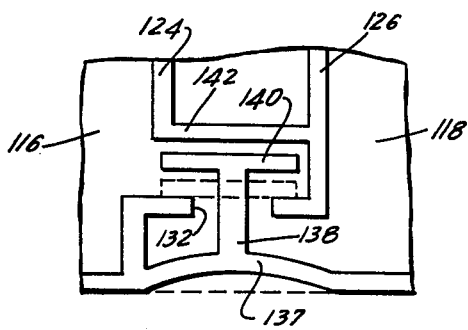

The modified form of the cuvette shown in FIG. 16 is similar in many respects to that shown in FIG. 15 and like reference numerals designate like parts. In the form of FIG. 16 the cuvette body has a bottom which in the central region has an upwardly deflectable portion 137 which normally occupies the broken-line position thereof and which carries on an upstanding post 138 integral therewith a valve member 140 normally closing the orifice 132. The bottom 142 of the central chamber is rigid. When it is desired to mix the contents, not shown, of chambers 116 and 118, the bottom portion 136 is deflected upwardly by a force moving the valve 140 to open position. The bottom portion 137 is maintained in this position during mixing of the contents of the aforementioned chambers 116 and 118.

Figure 17:
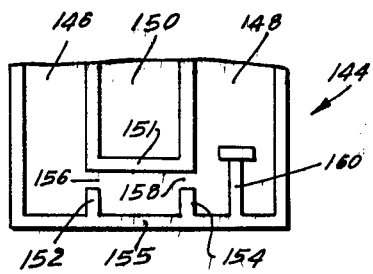

In the modified form of the cuvette shown in FIG. 17, the body 144 thereof defines a first chamber 146, a second chamber 148 and a central chamber 150. The bottom of the body 144 has laterally spaced, upstanding stub partitions 152, 154 thereon which respectively define therebetween and the continuous bottom 151 of the chamber 150 capillary-sized passageways 156, 158 in communication with each other and with the chambers 146, 148 for forced flow of the liquid contents (not shown) of the chambers therethrough on mixing in the above described manner with reference to FIG. 1. There is provided in the chamber 148 by way of example, an upright post or finger 160 integral with the bottom 155 of the cuvette body and having an enlarged head at the upper end thereof. This post 160 provides an anchor for the lyophilized or freeze-dried material in the chamber 148 to effectively tend to prevent any solid reagent, not shown, in the chamber 148 which adheres to the post 160 from comingling and mixing with the solid reagent, not shown, in the chamber 146. Moreover, during mixing of the liquid contents (not shown), the post 160 provides a baffle which enhances turbulence in the liquids being mixed, and thereby lends itself to the mixing action.

Figures 18, 19:
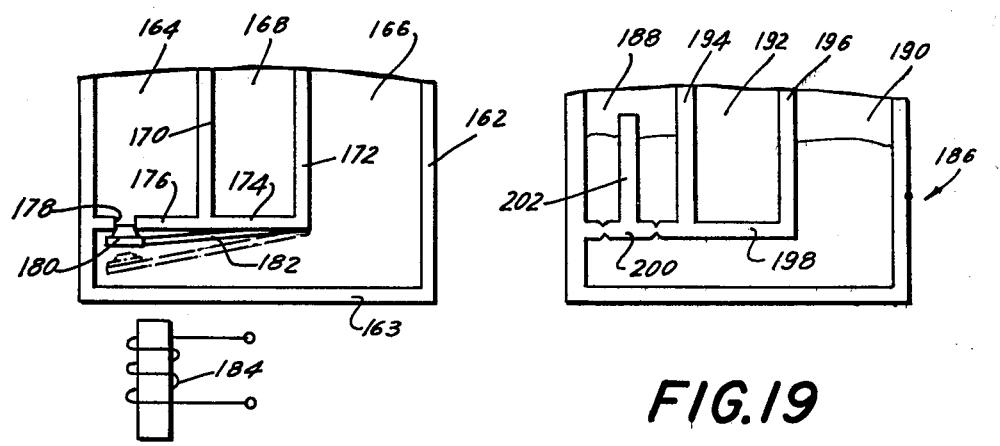

In the modified form of the cuvette shown in FIG. 18, the body 162 of the cuvette defines a first chamber 164, a second chamber 166 and a central chamber 168. Such chambers are separated by partitions 170 and 172. The partitions 170 and 172 have integral therewith, forming the bottom 174 of the central chamber 168, lateral extensions which merge with one another. One side of the cuvette body 162 and the partition 170 have integral merging lateral extensions forming a bottom 176 of the chamber 164 and defining an orifice 178 therethrough which, when open, provides fluid communication between the first chamber 164 and the second chamber 166 above the bottom 163 of the cuvette body. A valve member 180 cooperates with the orifice 178 to normally close the same and prevent such communication. The valve member 180 is formed of magnetic material and is supported as on a reed 182 from the bottom 174 of the chamber 168. For enabling mixing as in the form of FIG. 1 of the fluid contents, not shown, of the first and second chambers 164 and 166, respectively, the valve 180 is moved from its closed full-line position to the open position thereof shown in broken-line on energization of an electromagnet 184 located below the bottom 163 of the cuvette body in the vicinity of the valve member 180.

In the modified form of the cuvette shown in FIG. 19, the body 186 of the cuvette defines a first chamber 188, a second chamber 190 and a central chamber 192, the body having partitions 194 and 196. The partitions 194, 196, which are vertically arranged have merging internal lateral extensions forming the bottom of the chamber 192, the bottom being indicated at 198. One side of the body and the partition 194 have integral lateral extensions which merge with one another and provide in the central region thereof a frangable septum 200 having integrally formed therewith an upwardly directed post 202. Liquids in the first and second chambers 188 and 190, respectively, are maintained in isolated condition. When it is desired to mix these liquids the post 202, which extends above the liquid level in the chamber 188, is depressed by the application of force thereon without contaminating such liquid, causing the frangable septum 200 to break, allowing the liquids in the two chambers to mix. Such liquids may be mixed as in the form of FIG. 1. The cuvette of the form of FIG. 19, like the forms of FIGS. 14–18, has a suitable viewing window, not shown, for viewing the reaction in the cuvette.

As previously indicated by reference to the minute liquid volumes contained by the cuvette of the invention, the cuvette is relatively small. To further illustrate the size of the cuvette, the liquid sample volumes may be as small as 10–50 microliters.

While several forms of the cuvette have been illustrated and described, it will be apparent, especially to those versed in the art, that the cuvette may take other forms and is susceptible to various changes in details without departing from the principles of the invention.

What is claimed is:

1. A cuvette comprising a body member including means defining two distinct chambers, a pair of windows defined in at least one of said chambers for viewing the optical density of the contents thereof, each of said chambers defining at corresponding ends an opening through which reactants may be selectively introduced into said chambers, means defining a fluid passageway interconnecting opposite ends of said chambers and normally isolating liquids when contained in each of said chambers, the opening of at least one of said chambers being adapted and arranged for being in operative communication with a pressurizing means to enable forced-fluid flow along said passageway in opposite directions and between said chambers, so as to effect mixing of the liquids contained in said chambers, and means for sealing the openings of said chambers, said sealing means comprising a probe-puncturable plural-ply structure, one ply comprising a moisture-absorbent material.

2. A cuvette as defined in claim 1, wherein said body member is formed of a plastic material.

3. A cuvette as defined in claim 1, further including means for sealing the openings of said chambers.

4. A cuvette as defined in claim 1, further including means for sealing the openings of said chambers, said sealing means being probe-puncturable and self-sealing with reference to being punctured by a probe.

5. A cuvette as defined in claim 1, wherein at least a portion of said passageway is of capillary size to preclude fluid flow between said chambers.

6. A cuvette as defined in claim 1, wherein said passageway defines an air lock.

7. A cuvette according to claim 1, further including lyophilized reagents in at least one of said chambers.

8. A cuvette according to claim 1, further including a lyophilized reagent in at least one of said chambers, and means for anchoring said lyophilized reagent.

9. A cuvette as defined in claim 1, wherein said pressurizing means are adapted to alternately apply positive pressure and negative pressure to at least one of said chambers, to effect the mixing of said liquids.

10. A cuvette as in claim 1, further including a physical obstruction in said passageway to preclude fluid flow between said chambers, such obstruction adapted to be displaced to allow mixing of fluids between said chambers.

11. A cuvette as defined in claim 10, wherein said obstruction comprises a frangible septum.

12. A cuvette as defined in claim 10, wherein said obstruction comprises a valve member.

13. A cuvette as defined in claim 10, wherein said obstruction comprises a valve member formed of magnetic material and supported by a flexible member, said valve member being responsive to an external magnetic field.

* * * * *